United States Patent [19]

Hadden et al.

[11] Patent Number: 4,476,706
[45] Date of Patent: Oct. 16, 1984

[54] REMOTE CALIBRATION SYSTEM

[75] Inventors: David M. Hadden, Los Altos; Eric S. Micko, Los Altos Hills, both of Calif.

[73] Assignee: Delphian Partners, Sunnyvale, Calif.

[21] Appl. No.: 340,074

[22] Filed: Jan. 18, 1982

[51] Int. Cl.³ .............................................. G01N 27/12
[52] U.S. Cl. ..................................................... 73/1 G
[58] Field of Search ..................... 73/1 G, 23; 422/94, 422/96, 98; 340/632, 633, 634

[56] References Cited
U.S. PATENT DOCUMENTS
4,305,724 12/1981 Micko .................... 422/94

FOREIGN PATENT DOCUMENTS
649984 4/1979 U.S.S.R. .............................. 73/1 G

OTHER PUBLICATIONS
512 *Combustible Gas Detection*, Delphian Corporation, pp. 1-29, Jan. 1980.

Primary Examiner—Stephen A. Kreitman
Attorney, Agent, or Firm—Fitch, Even, Tabin & Flannery

[57] ABSTRACT

Methods and apparatus for remote calibration of combustible gas detectors in which calibration initiation signals are applied to a sealed, explosion-proof sensor assembly to effect a remote calibration sequence and storage of calibration factors.

10 Claims, 8 Drawing Figures

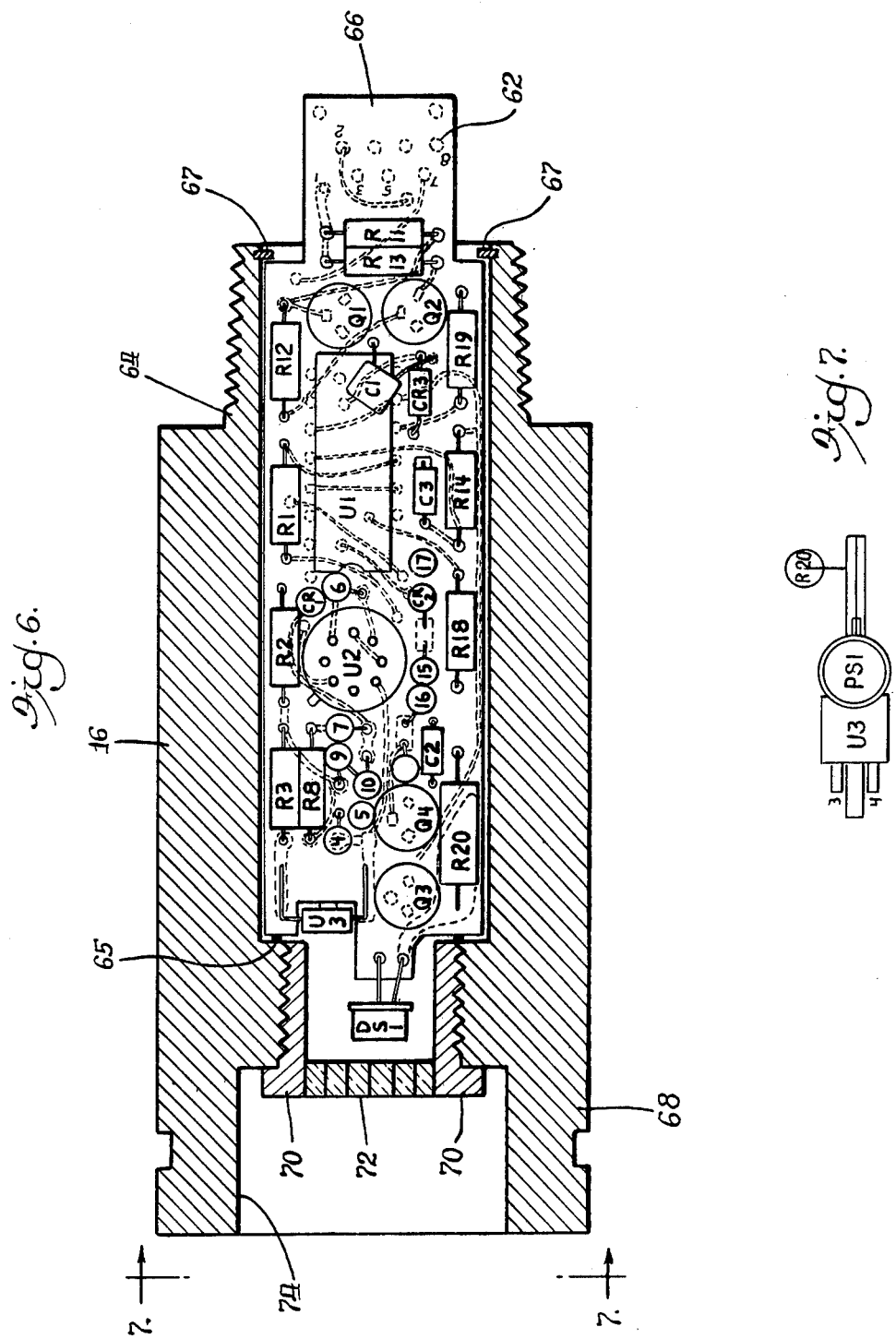

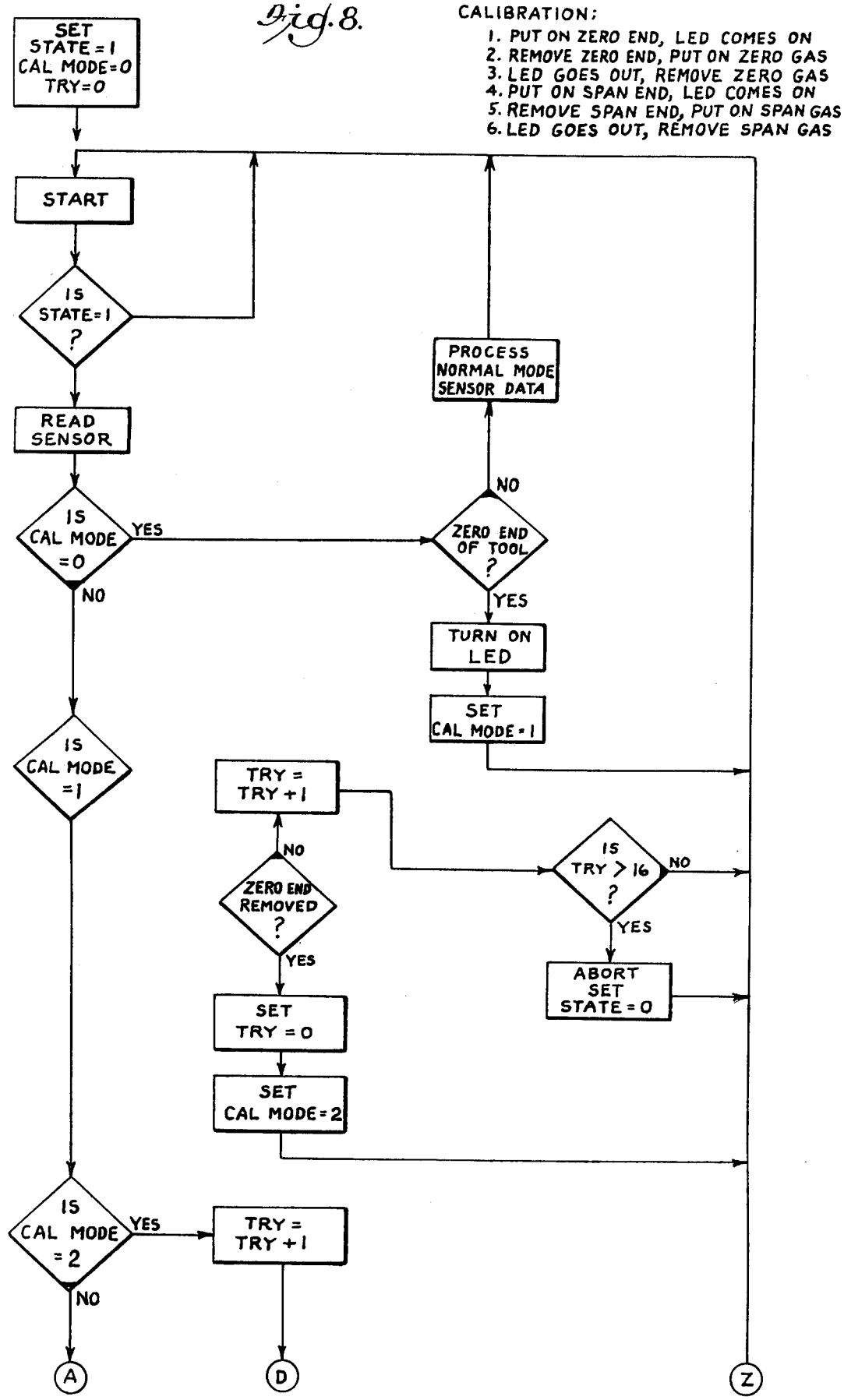

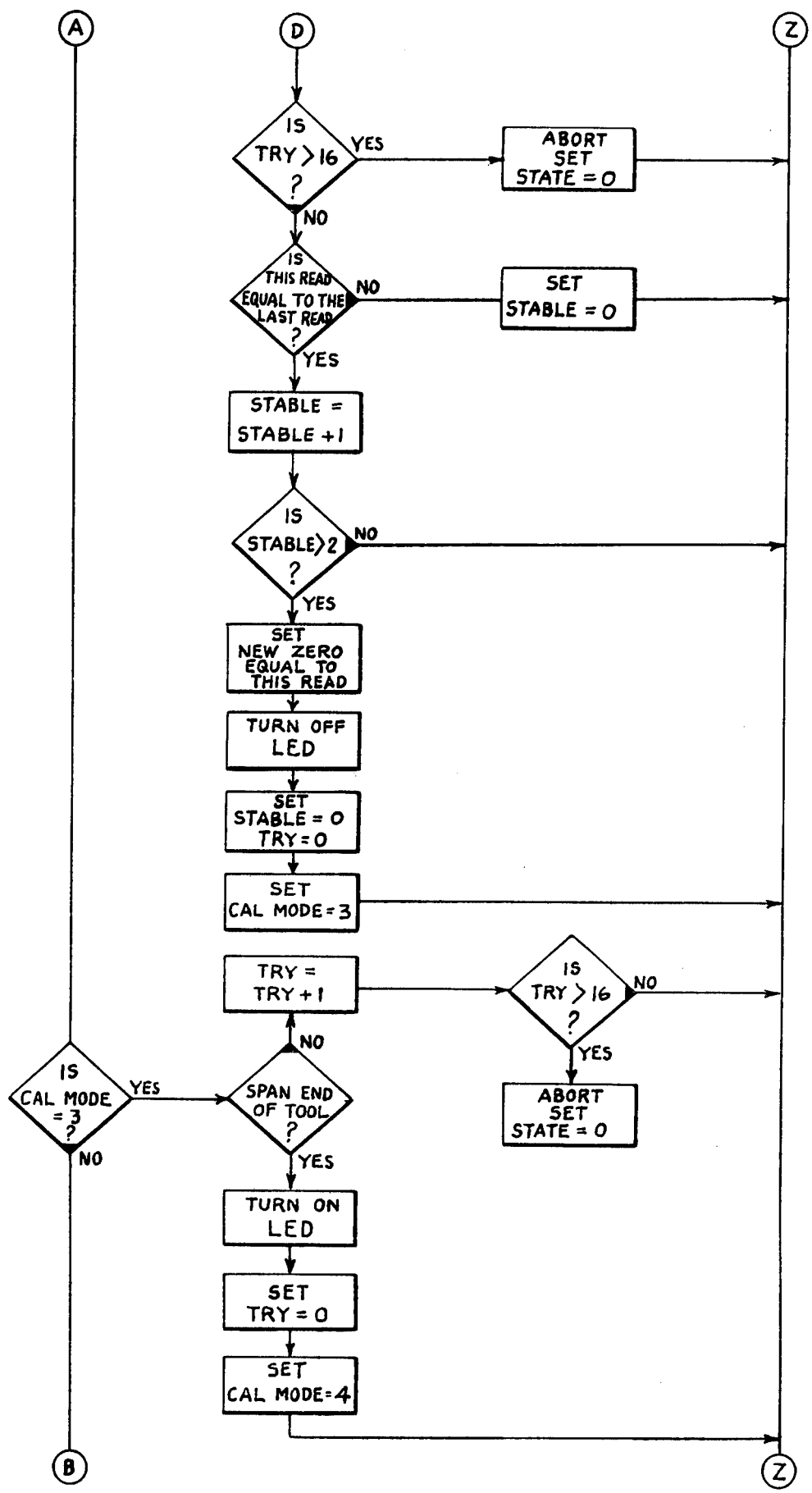

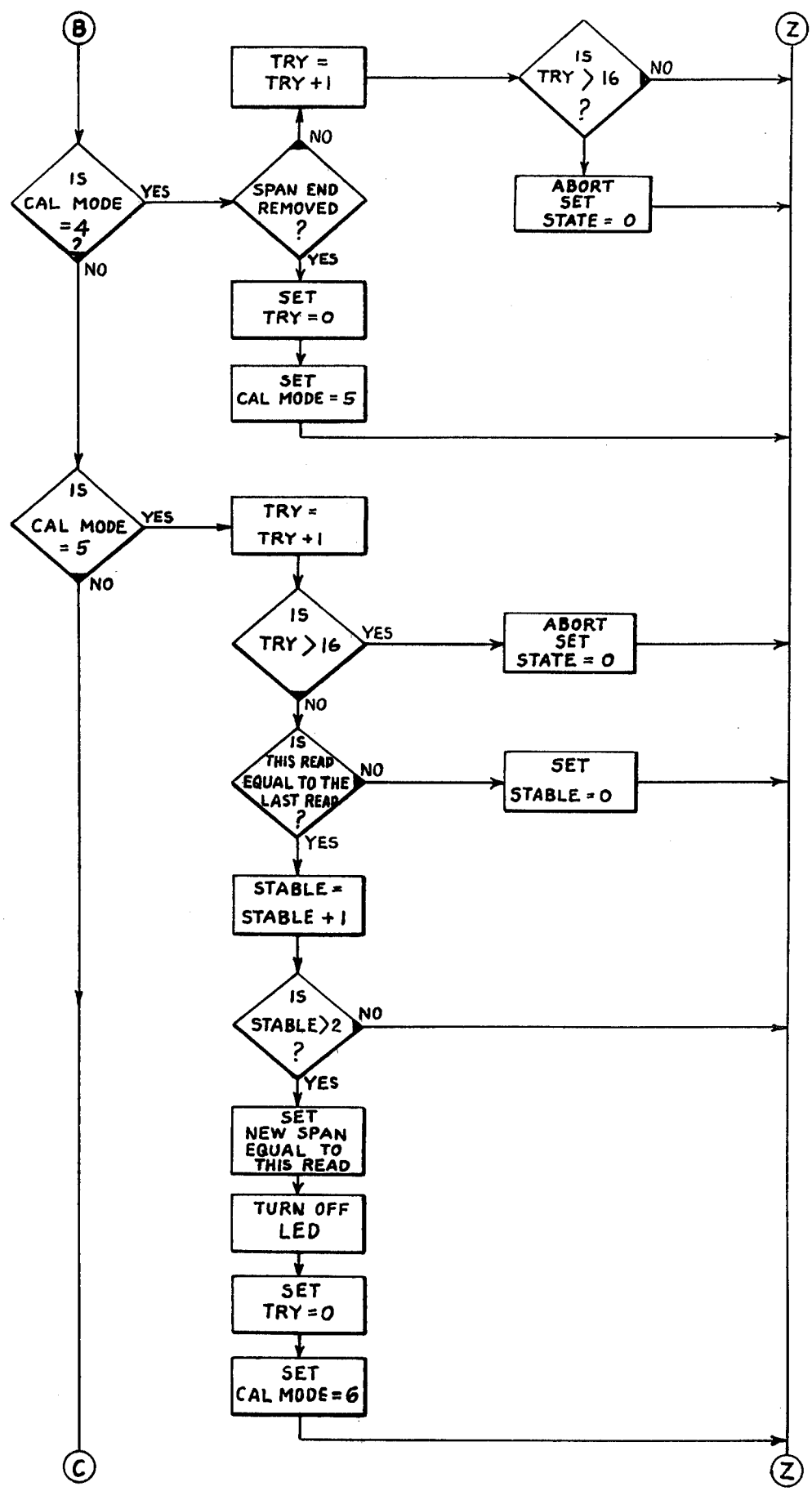

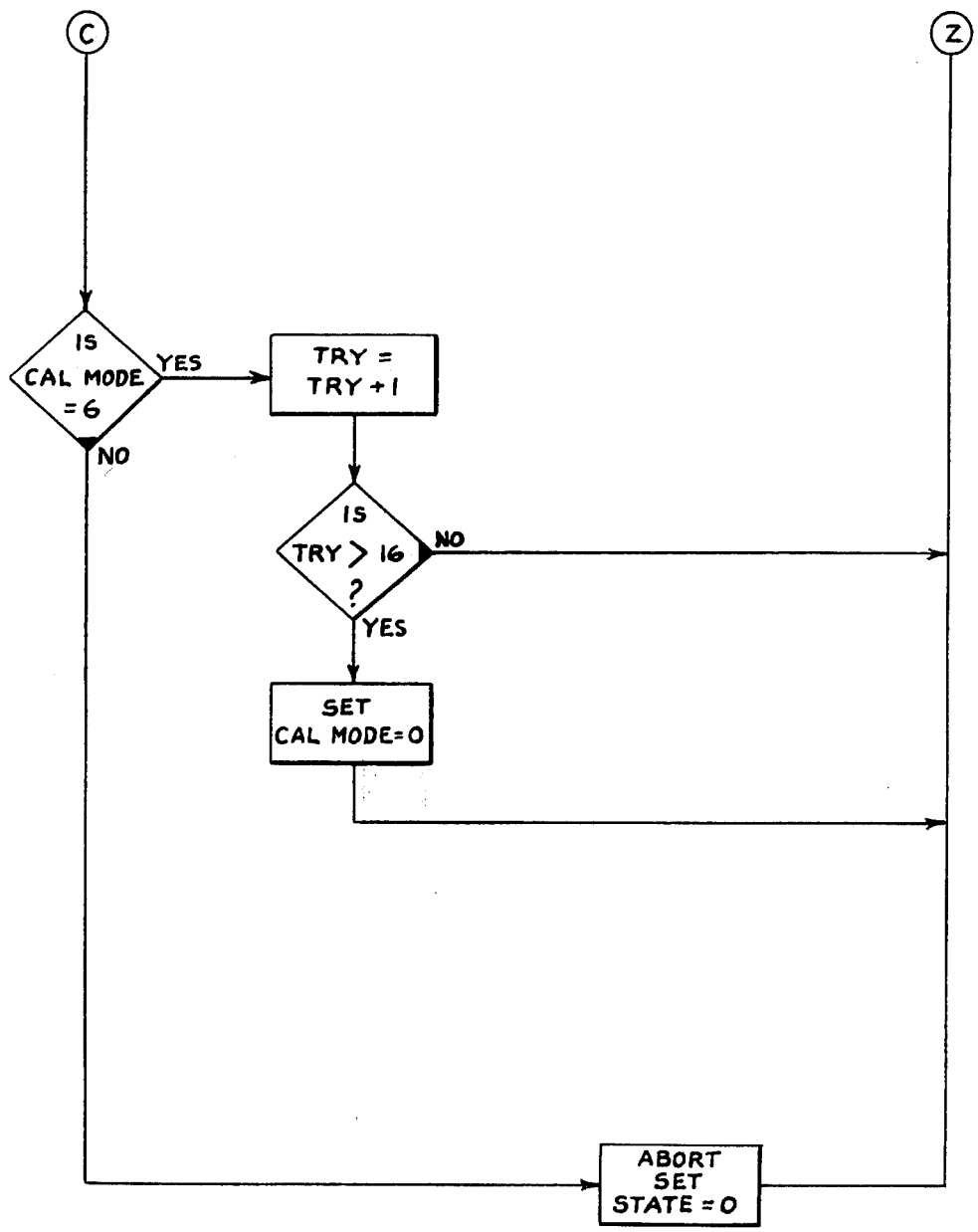

REMOTE CALIBRATION SYSTEM

Generally, the present invention is directed to measurement systems, and, more particularly, is directed to remote calibration systems including remote calibration methods and apparatus for detection and measurement of combustible hydrocarbons.

In many types of measuring systems an output, or controller device is located at a substantial distance from a related sensing or transmitter portion of the instrument, which in turn may be exposed to undesirable working or operating conditions. In this regard, the sensor device may be continuously or intermittently subjected under normal operating conditions to hazardous concentrations of flammable gases or vapors resulting from repair or maintenance operations, leakage, breakdown or faulty operation of equipment or processes. In addition to providing difficulties for calibration of the sensor devices, such on-site conditions may also cause failure of electrical equipment.

Sensor calibration is important to achieving accurate measurement from the sensor, because most sensors tend to have some zero drift over time in either the positive or negative direction, even when no combustible hydrocarbons are present. A similar problem exists with respect to the sensor span signal. Combustible hydrocarbon sensors have a tendency to slowly lose sensitivity with time. This loss of sensitivity may be corrected for by periodic span calibrations, in order to obtain a desired proportionality between the output signal and the combustible gas concentration monitored by the sensor device.

Accordingly, it is conventional to periodically calibrate the zero and span performance of remote monitor sensors in order to reconfirm or reestablish their measurement accuracy. Such calibration in the past had utilized two technicians, one located at the remote site with a walkie-talkie and a portable gas detection instrument, and the other at the central controller. The remote-site technician would first use a portable gas detector to make sure no combustible hydrocarbons are present so that it was safe to use a walkie-talkie. The technician would then inform a technician at the central controller station to which the sensor signal is directed to "zero" the sensor at the controller. Subsequently, the remote-site technician would then apply a known concentration of combustible gas to the sensor, and the controller operator would then adjust the readout appropriately for that remote sensor unit. The process would be repeated for other remote sensors connected to the central controller. Where substantial concentrations of combustible gas existed, however, it was not possible for the technician to use a walkie-talkie, and either the area had to be cleared of all combustible hydrocarbons, or the technican would need to find other communication devices or remove himself to an area where it was safe to use a walkie-talkie. While this was an acceptable calibration method, it is relatively costly and inefficient.

Provisions for calibration of gas detection equipment at the sensor site have more recently been developed in the art which utilize electronic remote calibration techniques. Combustible gas detection equipment may be conventionally provided with some form of one-man remote calibration capability, for example, in which an operator goes to the remote site and makes sure that no combustible hydrocarbons exist using a portable gas detector. The operator may then remove the cover to the transmitter portion of the remote gas detection device to expose a volt meter receptacle, a "zero" potentiometer and a "span" potentiometer for making respective "zero" and "span" calibrations. After making the "zero" adjustment, a known concentration of calibration gas is applied by the operator to the sensor for adjustment of the span calibration until the appropriate reading is obtained. The cover may then be replaced, the calibration gases removed, and the cycle repeated for a subsequent sensor device.

While this technique is a substantial improvement over the earlier two-man calibration procedure, there is still a substantial need for improved methods and apparatus for remote calibration of sensor instrumentation for potentially hazardous locations. For example, it is a substantial disadvantage that a cover must be removed from the transmitter to expose the internal calibration controls, in view of safety considerations. In this regard, equipment operated in various areas classified as hazardous must be operated in "explosion-proof" enclosures designed to meet specified safety criteria. Although such enclosures may be opened by first declassifying the area using a portable combustible gas detection instrument, it will be appreciated that the opening of such explosion-proof enclosures is generally undesirable. Further, removing the cover to the sensor box may expose internal electronic components to undesirable environments such as humidity, snow, rain, corrosive gas or dust, which may adversely affect the integrity or performance of the sensor units, particularly after repeated calibration cycles.

In this regard, the "zero" and "span" potentiometers are particularly vulnerable to contamination failures. Moroever, in some hazardous areas there is a continuous presence of combustible hydrocarbons, which may be above the lower flammable limit of that gas or vapor. Under these conditions, it is not possible to remove the cover from an explosion-proof box, necessitating the inefficiency and complications of manual "synchronized-watch" or similar techniques utilizing both "zero gas" (e.g., pure air) and "span gas" in a timed calibration technique.

It is also desirable to reduce the potential for human error by improper setting of calibration readings. Moreover, the utilization of manual calibration tends to limit the places in which remote sensors may be located without presenting difficulties to the operator in carrying out the calibration procedure.

Accordingly, it is an object of the present invention to provide improved methods and apparatus for remote calibration of sensors for measurement and detection of combustible gases or other hazardous materials. This and other objects of the present invention will become more apparent from the following detailed description and the accompanying drawings, of which:

FIG. 6 is a cross sectional view of the remote calibration housing of the embodiment of FIG. 1, illustrating the construction of the housing and enclosed circuit board assembly;

FIG. 7 is an end view of the circuit board assembly enclosed by the remote sensor housing of FIG. 6; and FIG. 8 is a flow chart depicting controller function in remote calibration operation of the embodiment of FIGS. 1 and 2.

Figure 1:
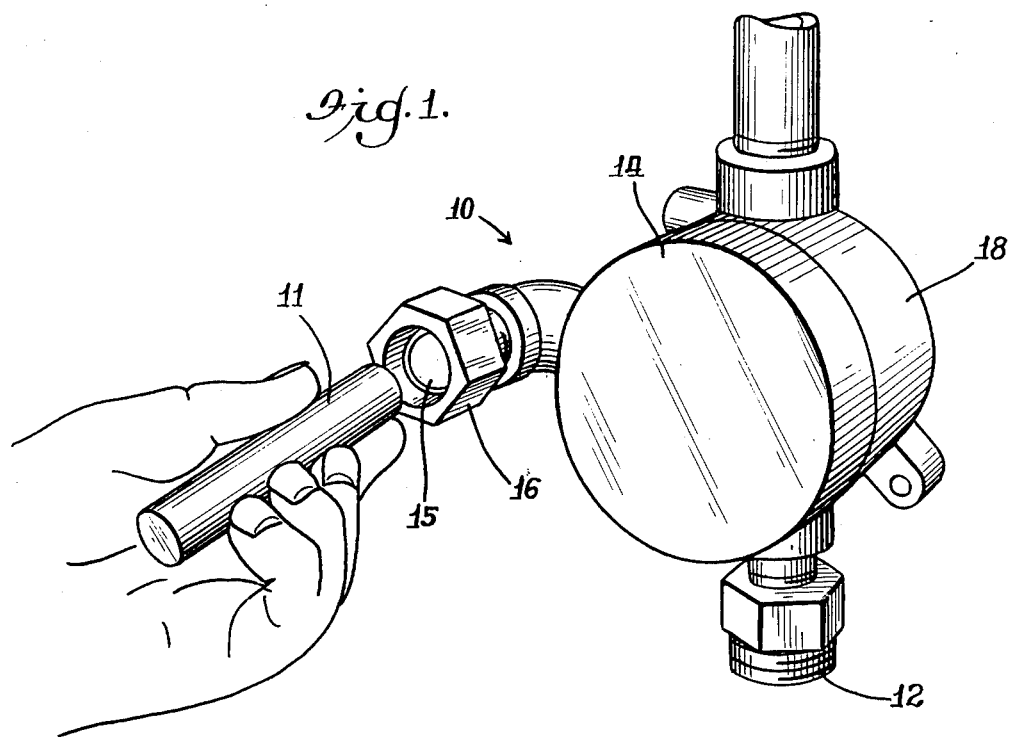
FIG. 1 is a perspective view of an embodiment of a combustible gas sensor, remote calibration sensor and transmitter in accordance with the present invention.

Generally, in accordance with the present invention, methods and apparatus are provided for remote calibration of sensor telemetry instrumentation such as combustible gas dectors or the like. Further in accord with the invention, such methods and apparatus which are adapted to provide a calibration mode of operation by means of which appropriate calibration factors such as baseline (i.e., "zero") and sensitivity response (e.g., "span") factors may be obtained on demand for retention and subsequent application to sensor output.

In this regard, apparatus in accordance with the present invention includes means for sensing the output signal of a combustible gas detector or the like, and means for determining whether such output signal is within a predetermined operative signal range for the combustible gas detector. The combustible gas detector apparatus will include means for transmitting a signal, desirably over a shielded transmission cable, to a remote controller, which is representative of the combustible gas concentration detected by the combustible gas sensor. Desirably, this signal may be an analog current signal proportional to combustible gas concentration over a predetermined signal current range. The apparatus advantageously includes detector fault signal means for transmitting a signal to a controller when the detector signal is not within the predetermined range. Desirably, the detector fault signal may be a unique current level signal outside the normal operating range of the combustible gas current signal transmitted to the controller. The combustible gas detector may desirably utilize a catalytic gas detection element in Wheatstone bridge arrangement to provide an output signal current or voltage which is a function of combustible gas concentration, although various other types of detection instruments such as optical (IR) detectors having such an output signal may be utilized. The apparatus further includes signal generation means for generating and transmitting a zero calibration initiation control signal to a control station. Desirably, the zero initiation signal will be a unique current-level signal outside the normal operating range of the combustible gas signal, and distinct from the sensor fault signal. The zero control signal generation means desirably comprise means for detecting the initiation of a zero calibration cycle by an operator external to the apparatus, and may preferably comprise a magnetic "Hall Effect" switch activated by application of an appropriate magnetic field thereto. However, such means for initating the zero calibration control signal may also comprise circuit components other than a magnetic "Hall Effect" switch-magnetic system. For example, magnetic reed switches, mechanical switches appropriately isolated from the remote calibration circuitry, appropriate light and photo detector systems, capacitance switches, or inductive detector circuits may similarly, although less desirably be utilized.

The apparatus further includes signal generation means for generating and transmitting a span calibration initiation control signal to a control station. Desirably, the span initiation signal may be a unique current-level signal like, but distinct from the zero initiation signal. The span control signal generation means similarly desirably comprises means for detecting the external application of an operator signal for initiation of a span calibration cycle, and may desirably comprise circuit components like those of the zero calibration means. Desirably, as will be appreciated from the subsequent disclosure, the span control signal generation means is responsive to a different externally applied signal than the said zero control signal generation means.

Further, the system includes means for receiving a zero calibration acknowledgement signal and a span calibration acknowledgement signal from a control station, and may desirably further include means for displaying receipt thereof to an operator. The means for receiving such zero and span acknowledgement signal may further function to activate the span signal generation means, so that calibration of the instrument may proceed only upon the successful completion of the preceeding calibration step.

Further in accordance with the invention, control console means for receiving output signals from the remote calibration means may be provided, which is adapted for detecting and distinguishing among sensor concentration, sensor fault, zero calibration and span calibration control signals from the remote calibration means.

The control console means should be adapted to transmit zero and span acknowledgement signals and to store, respectively, a zero gas signal value and a span gas signal value transmitted from the remote gas detection means after detection of the respective zero and span initiating signals from the remote calibration means, and to apply correction factors based on these stored values to the signal received from the remote gas detection means, as will be described in more detail hereinafter. Desirably, the acknowledgement signals may be AC signals superimposed on the current-level signals received from the sensor/transmitter apparatus, which accordingly may be transmitted over the same transmission line as the sensor/transmitter DC current-level signals.

Having generally described apparatus aspects of the present invention, the invention will now be more particularly described with reference to the remote combustible gas detector embodiment 10 shown in FIGS. 1–7 of the drawings. As shown in FIG. 1, the embodiment 10 comprises a sensor element module 12, a transmitter module 14, and a calibration module 16 disposed in an explosion proof electrical housing 18 of conventional construction. The entire unit 10 is sealed against propagation of explosions from within, and communicates with and receives electrical power from a remotely located control unit and power supply by a three wire cable. The sensor and various transmitter components of the embodiment 10 of the illustrated embodiment are generally in accordance with the disclosure of U.S. Pat. No. 4,305,724 issued Dec. 15, 1981, which is incorporated herein by reference. As will be discussed in further detail in respect to FIGS. 6 and 7, the external surface of the calibration module 16 is of compact, explosion-proof construction which permits magnetic field penetration to initiate zero and span calibration of the combustible gas sensor. The module 16 houses a first magnetically activated switch operative by application thereto of one magnetic pole of an appropriate magnetic tool 11 for initiation of a zero calibration, and a second, spanning, magnetically activated switch operative by application thereto of the opposite magnetic pole of the magnetic tool 11. The calibration module 16 further includes light emitting diode for signaling the operator upon receipt of an appropriate signal from a control station as will be more fully described hereinafter.

Figure 2:
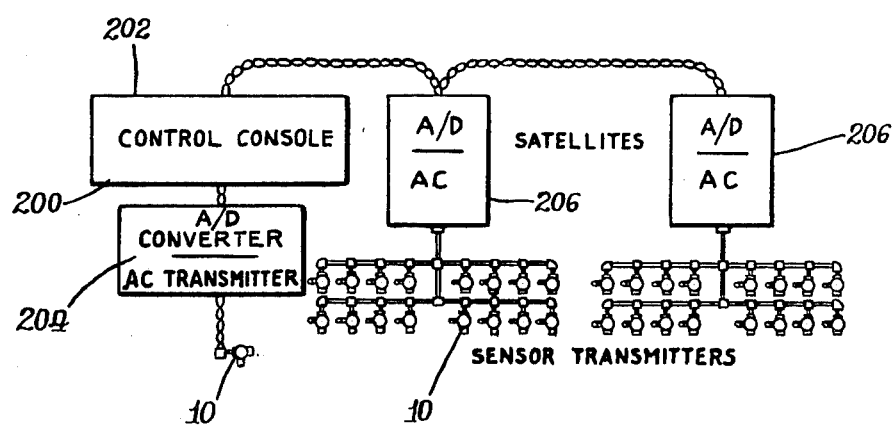
FIG. 2 is a schematic diagram representing various of the circuit elements of a remote calibration system embodiment utilizing a plurality of sensor transmitters of the type illustrated in FIG. 1.

As shown in FIG. 2, one, or a plurality of gas detector units 10 may be in operative connection (by means of direct wire connections, radio connection or combinations thereof) to a control console 200, which in the illustrated embodiment includes a digital processor 202 and one or more A/D converter and AC transmitter stations 204. Multiple arrays of sensor transmitters 10 may be connected to a digital control console 202 by means of appropriate distributed processing devices such as A/D and AC signal generating satellites 206, as illustrated in FIG. 2. The control console may include appropriate microprocessor components, and circuitry for receiving and interpreting the signals from the A/D converter 204 and/or 206, and for generating appropriate command signals to the devices 204, 206 for generating AC signals to the sensor units 10, as will be further described. In the illustrated embodiment, information is transmitted from the combustible gas detector units 10 as current signals in which the current level reflects information relating to detected combustible gas levels or remote instrument calibration and accordingly, the signal interpretation system of A/D converter components of elements 204 and/or 206 include means for converting the current signals to voltage representation and subsequently to digital form for storage and/or interpretation by the control console 200. The current-to-voltage converter and analog-to-digital conversion circuitry may be provided in accordance with conventional practice. The conversion of the current-signal information from the sensor units 10 to digital form provides economy of information transmission, processing and storage, and will become more apparent hereinafter. The provision of satellite units 206 for individually converting the current signals of a plurality of sensor units 10 to digital signals provides for convenient multiplexing and addressing of information between controller 202 and the individual sensor units 10. The A/D converter units 204, 206 are provided with appropriate means for digital communication with the controller 200, in accordance with conventional digital processor art. It will be appreciated that a large number of sensor units 10 may be addressed and operated by the console 202, which in turn may also store and address for processing, the appropriate digitized signal values for the individual sensor unit.

Further, in the illustrated embodiment 10, the illustrated remote calibration sensor unit 10 is responsive to AC signals from the controller 200, and accordingly the console 202 and A/D converter and AC generating units 204, 206 are provided with means responsive to digitally transmitted signal from the console 200 for generating and transmitting an AC zero or span acknowledgement signal to the individual sensor units 10 addressed thereby. The controller is provided with appropriate means for causing the AC transmitter circuitry of units 204 and/or 206 to generate such signals. Such apparatus may utilize conventional AC signal generating components for generating and addressing components. Appropriately software for utilization by the console 200 is depicted in FIG. 8.

Having generally described the remote calibration system including aspects of the present invention, each of the components will now be specifically described.

As indicated, the embodiment 10 includes a combustible gas detection sensor system, which provides an output signal responsive to the presence of combustible gas. The circuit embodiment 300 of the illustrated combustible gas detector is shown in FIG. 3, which will be described hereinafter.

Figure 3:
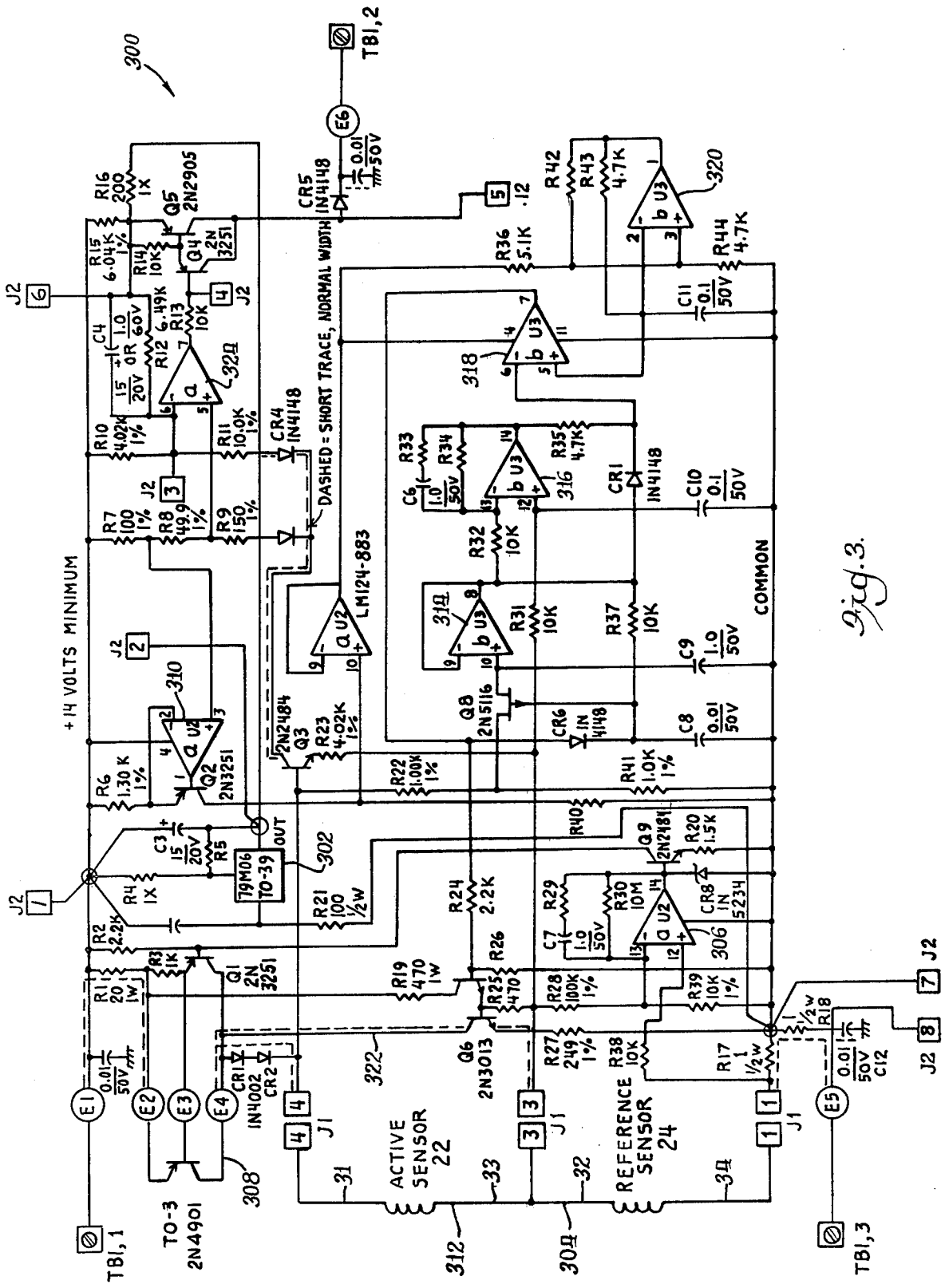
FIG. 3 is a circuit diagram of an embodiment of combustible gas detection circuitry utilized with the embodiment of FIG. 1 illustrating the circuit components thereof and the manner of their interconnection.

Also provided in the circuitry 300 is a current measuring resistor R18 intended for measurement of the current flowing in the combustible gas detector circuitry 300, and capacitors C1, C5 and C12 which are for suppression of noise that could otherwise come into the transmitter 300 (FIG. 3). Further incuded are transmitter terminal connections indicated by terminals identified on FIGS. 3 and 5 by boxes designated 1-8, respectively, which form one communication channel to the remote calibration system 400 (FIGS. 4, 5) which will now be more particularly described.

Figure 4:
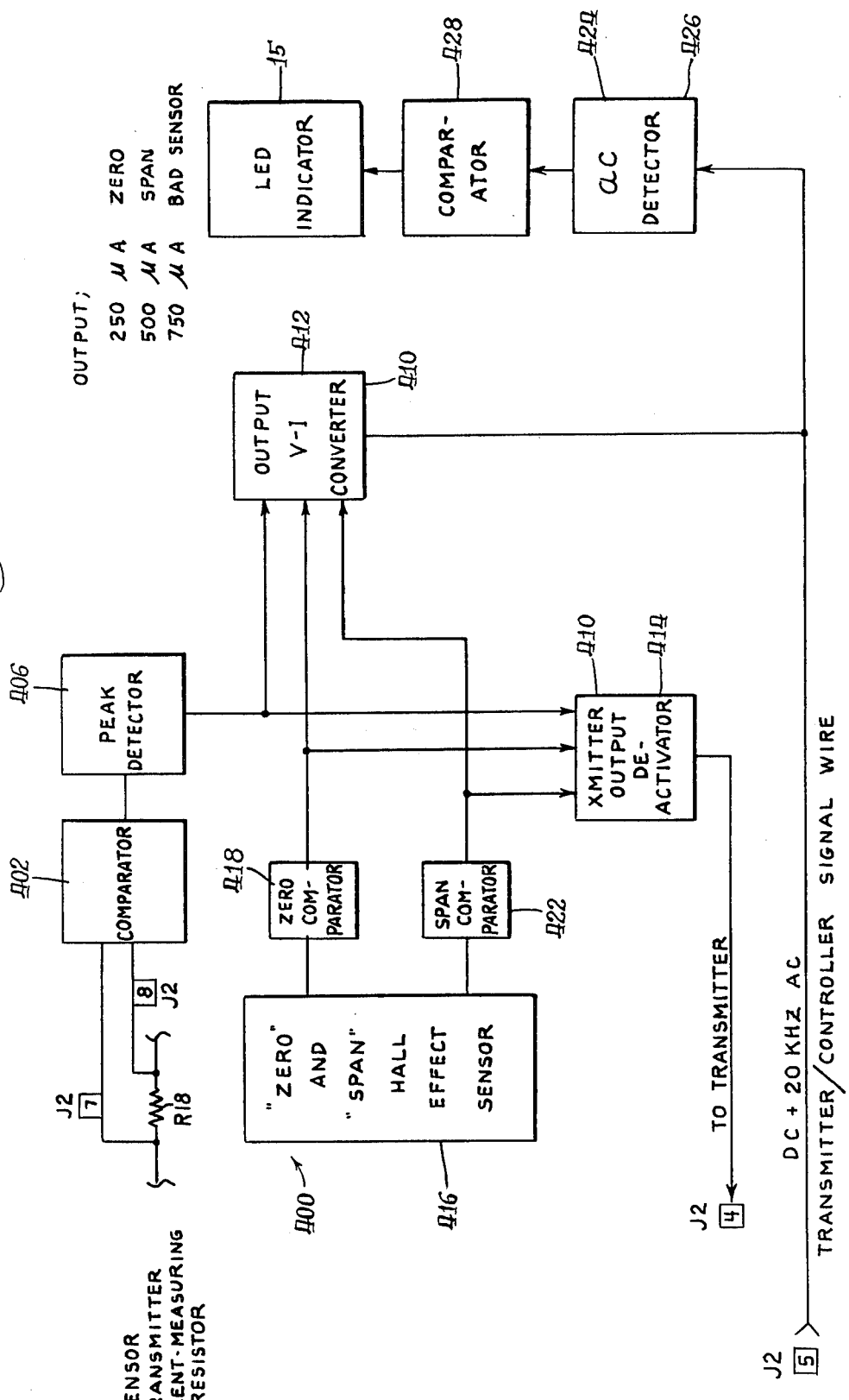
FIG. 4 is a block diagram of the remote calibration circuitry of the embodiment of FIG. 1.
Figure 5:
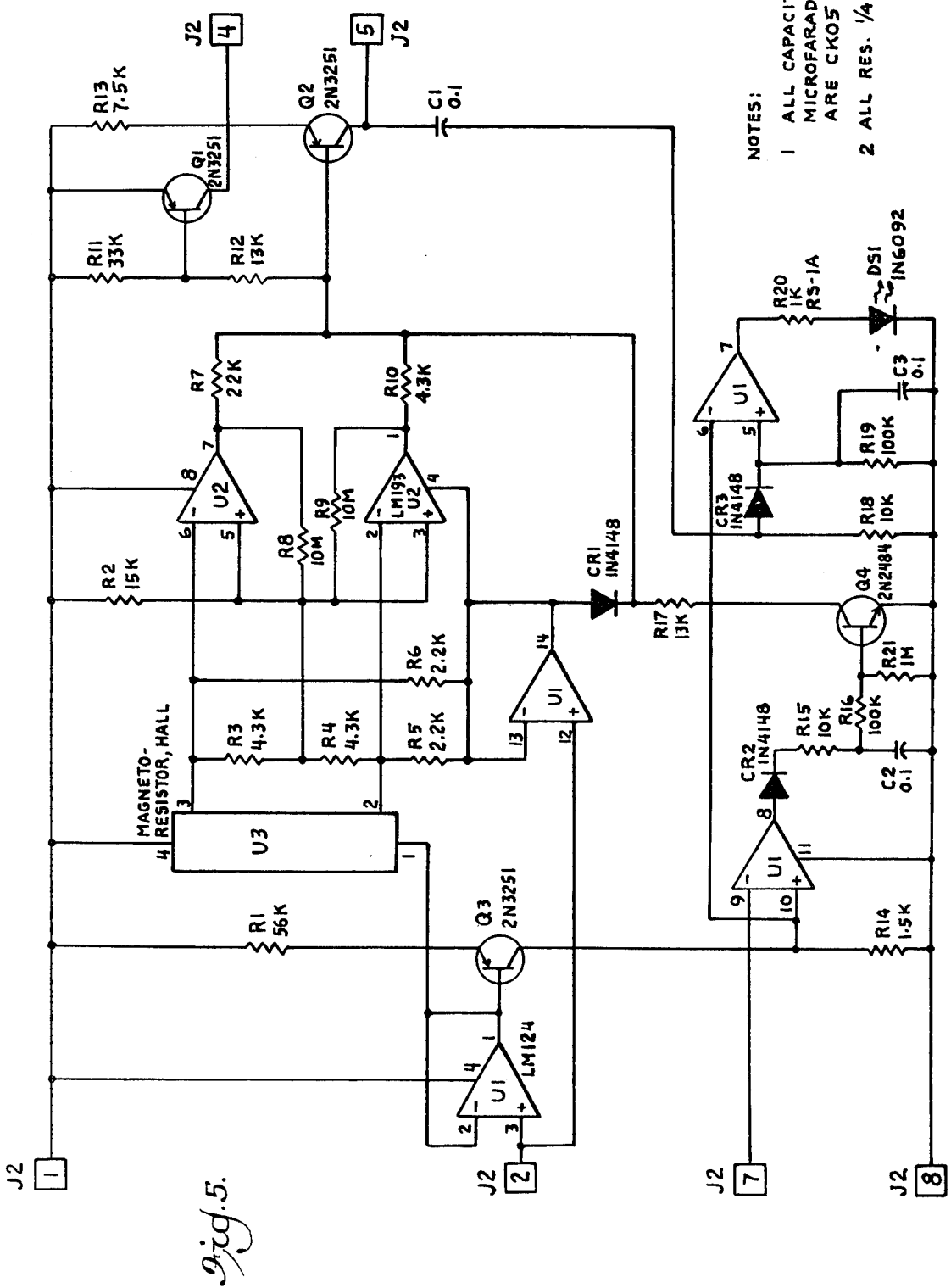
FIG. 5 is a circuit diagram of the remote calibration circuitry of the sensor transmitter of FIG. 1.

Unless overridden by the remote calibration circuitry of the device 10, shown in FIGS. 4 and 5, the illustrated sensor/transmitter circuitry 300 will transmit a current signal to the controller 200 via the satellite 206 in a predetermined range of 4 to 20 milliamperes representative of combustible gas concentration sensed at the unit 10. The current signal output at zero combustible gas concentration is nominally 4 milliamperes (with generally linear increase in output current with increasing combustible gas concentration) and the circuitry 300 will not generate less than 1 milliampere of output signal unless the circuitry is defective. The current signal to the controller 200 via the satellite 202 is operated outside of the 1-20 mA current range to carry out remote calibration of the sensor/transmitter 10, as will be more fully explained.

As indicated, the current output signal from the gas detection circuitry 300 is transmitted to the controller 200 unless overridden by the remote calibration circuitry 400 of FIGS. 4 and 5. In this regard, with reference to the functional block diagram of FIG. 4, the input function of the illustrated remote calibration circuitry 400 has three information input channels, each of which will cause overriding of the normal transmitter to controller signal. These three input channels, which can cause overriding of the transmitter controller signal, will each substitute for the normal 1-20 signal, a signal which corresponds to the particular input which has been activated. The control console 200 can distinguish the plurality of such inputs and thereby receive and respond to a number of different types of information from the remote calibration terminal 10.

Because zeroing and spanning calibration values obtained from the sensor output signal for each sensor/transmitter unit 10 are continuously determined and stored in the controller 200, appropriate signals are respectively transmitted to and from the remote calibration circuitry 400 to carry out such a calibration cycle.

As shown in FIG. 4, the remote calibration circuitry embodiment 400 comprises comparator means 402 for determining whether the sensor/transmitter supply current of the combustible gas detector circuitry 300 is within a predetermined range, indicating normal operation, which for the illustrated embodiment 400 is represented by a comparator measurement current of not less than about 150 milliamperes. The comparator 402 also connects to a peak detector 406 which receives input from comparator 402 and which functions to detect a faulty sensor condition caused by an inoperative sensor element causing a periodic signal in the operative range at the detector frequency of the circuit 300.

The circuitry 400 further includes means 410 for providing a plurality of current signals differentially representative of input channel conditions of the circuitry 400. In the illustrated embodiment, the means 410 comprises an output voltage-to-current (V-I) converter 412 and transmitter output deactivator 414. The sensor current comparator 402 and peak detector 406 determine when the sensor/transmitter current is outside the predetermined range of operability conditions, and provide input signals to both the output V-I converter 412 and the transmitter output deactivator 414 upon such condition. Upon receipt of such signal, the transmitter output deactivator 414 deactivates the transmission of the normal combustible gas concentration signal to the control console 200. Furthermore, upon receipt of such signal from sensor comparator 406 to output V-I (voltage-to-current) converter 412, the converter 412 converts the voltage level input from comparator 406 to a unique current signal level, which in the illustrated embodiment is a signal current level of 750 microamperes to signify an inoperative or "bad" sensor.

The remote calibration circuitry 400 further includes input channel means 416 for detecting the external application of an operator command to initiate a zero calibration or a span calibration of the unit 10. In the illustrated embodiment, the means 416 comprises a Hall effect sensor having outputs respectively sensitive to the application of "north" and "south" magnetic fields of a hand held permanent magnet 11. An output signal from means 416 responsive to the application of a "north" field sensed by zero comparator 418, which in turn directs a signal to V-I converter 412 and transmitter output deactivator 414, so that upon application of the "north" magnetic field to the sensor 418, the transmitter output is deactivated and a unique current signal, here a current signal level of 250 microamperes is transmitted to the A/D converter circuitry 204, 206 and from there is transmitted in digital form to the console 200 to indicate the initiation of a zero calibration.

The circuitry 400 further includes input channel signal means for detecting the external application of an operator command to initiate a span calibration of the unit 10. In the embodiment 400, the opposite "south" polarity sensing output of the means 416 is directed to a span comparator 420. Upon application of such opposite magnetic field, the span calibration comparator 420 provides a signal to the transmitter output deactivator 414 and the output V-I converter 412 to deactivate the combustible gas concentration current signal, and to generate a unique current signal, here a current signal of 500 microamperes to the control console 200 via the A/D converter of units 204, 206 to indicate the initiation of a span calibration.

The remote calibration circuitry 400 also functions to receive and display acknowledgement signals from the controller 200, and accordingly includes means 424 for detecting signals from the control console 200 via the AC generating circuitry of units 204 and/or 206, which in the illustrated embodiment are AC signals superimposed on the DC current signals between the satellite 204, 206 and the units 10. The means 424 in the illustrated embodiment comprises AC detector 426, comparator 428 and light emitting diode indicator 15 to signal to the operator the receipt of a signal from the control console to the unit 10. While a LED is utilized in the illustrated embodiment, it will be appreciated that other explosion-proof operator signalling devices could be used, such as a liquid crystal display, an earphone with inductive coupling, etc.

To initiate operation of the remote calibration cycle, one (e.g., the North) pole of a permanent magnet 11 is brought into close proximity of a magnetic field sensitive device such as a Hall effect device which is provided in the calibration module 16. The Hall effect device is designed in such a way that it is sensitive to the lines of flux flowing from the north pole of a magnet. Once the Hall effect device 418 is subjected to the north pole of a magnet, such as magnet 11, it immediately signals the remote calibration circuitry to disengage the 1–20 mA current signal from the sensor and replace it with a 250 microampere current signal.

Via the satellite 206 or A/D unit 204, the control console 200 recognizes this 250 microampere current as a signal for it to begin a zeroing procedure as will be more fully explained in respect to the flow chart of FIG. 8, and to send an acknowledgement signal back to the remote calibration device 10 to turn on the light emitting diode for observation by the operator. The magnet may be removed as soon as the LED begins emitting. The operator may apply a "zero" gas containing no combustible gases to the combustible gas detector sensor element, or may rely on an ambient zero reading from a hand-held detector. A continuously emitting LED indicates to the operator that the controller has received the zero command and is in the process of attempting to "zero" the sensor. The current response during zeroing is periodically sampled, converted to digitized form, and transmitted to the control console 200, where it is appropriately stored as "zero" if it is stable. Under normal conditions, in about one minute, the control console 200 will cause the continuously emitting LED to go out. This signals the operator that the zeroing operation has been successfully completed. In the event that the control console 200 is not able to zero the sensor, the continuously emitting LED changes to a blinking condition to advise the operator that adjustment may not be accomplished and the sensor should be replaced.

More sophisticated messages from the computer may be accomplished by generating more complicated flashing patterns to the remote calibration LED. The eye can easily distinguish between several duty cycles and/or flashing rates, such as 25, 50 and 75 percent duty cycle with a 3 cycle per second frequency when using red LEDs as the light source. One flashing mode may be used to indicate that the sensor is outside of an acceptable zeroing range, other flashing rates could be used to indicate problems in the transmitter, or digital values of measurement or other coded information Assuming that the control console 200 has successfully zeroed the sensor 10 output, the operator is now in a postion to begin the span calibration. First, the operator applies the appropriate span gas having a known predetermined concentration of combustible gas to the sensor module 12 using a standard calibration cup. The operator now places the opposite (e.g., south) pole of a permanent magnet 11 in close proximity to the calibration module 16 of the unit 10. The Hall effect device sensitive to this magnetic pole immediately causes the 1–20 mA current signal from the sensor circuitry 300 to be disengaged and a 500 μA signal to be installed in its place. The controller 200 recognizes that a 500 microampere current is the command to begin a span cycle. Its first response is to send a signal to the unit 10 to cause the LED 15 at the calibration device to continuously light. As in the case of the zero acknowledgement signal, this is carried out by transmitting an appropriate digital control signal to the unit 204 or 206, which addresses the desired sensor/transmitter 10, which responds by transmitting an AC acknowledgement signal to the desired unit 10 superimposed on the DC current signal from the unit 10. The magnet may be removed as soon as the LED beings emitting. Once an appropriate span calibration can be completed, the control console 200 will cause the continuously emitting LED to go out. This signals the operator that he can remove the calibration gas and that the calibration cycle for that sensor has been properly completed. It is of course possible to send more sophisticated signals to the operator indicating various failure modes at the sensor transmitter site, as previously discussed. It may also be desirable to have a plurality of span calibrations using different concentrations of calibration gas.

It is necessary for calibration gas to be applied to the illustrated sensor module 12 for a period of anywhere from about 30 seconds to about 2 minutes before a stable reading can be obtained, depending on various conditions of calibration. The signal from the sensor approximately follows a rising asymptotic curve. The control console 200 may be adapted to recognize from the sensor's response in the first few seconds how long it will take before a reading stable to within three or four percent of full scale will take place. Because of this, the controller will not signal the operator to remove his span gas until the sensor is appropriately stable and the controller has been properly span calibrated. The controller also desirably may be adapted to prevent a span calibration without a proper zero calibration having previously been carried out.

The ability of the controller 200 to control the appropriateness of span calibration of the sensor 10 removes one area of judgment from the individual making the calibration. On more conventional systems, the operator may, in error, not wait until a sensor has reached its maximum appropriate value for calibration before setting the span, thereby over-compensating for slow response time by increasing the span. While the illustrated embodiment 10 includes zero and span calibration capability, it will also be apparent that additional remote calibration cycles or procedures may be included so that field procedures in addition to zero and span adjustments may be performed through the establishment of appropriate current signal zones and appropriate controller signal recognitions.

As indicated, the unit 10 is responsive to signals from the controller 200. In this regard, the controller 200 causes the satellite signal units 204 and/or 206 to provide an AC control signal, which in the illustrated embodiment is a 20 kHz wave of four volts peak-to-peak amplitude which is superimposed on the normal transmitter-to-controller signal wire. This AC control signal does not affect the normal operation of the sensor transmitter, but is received by the remote calibration circuitry 400 as an instruction to turn on the LED 15. This provides the visual output function at the remote unit 10, as previously described. The specific embodiment of combustible gas detection apparatus is particularly suited for use with the remote calibration system 400. These specific circuit embodiments and their particular modes of operation will now be described in detail.

Illustrated in FIG. 3 is the circuit embodiment 300 of the gas detector circuitry of transmitter 12, and illustrated in FIGS. 4 and 5 is the circuit embodiment 400 of remote calibration circuitry, which circuits will now be described in detail. Power is supplied to the circuits 300, 400 from the satellite 204 or 206 over a wire providing at least +14 volts potential connected to TB1, 1 with ground return provided to a second wire between the satellite and TB1, 3. A third wire connection between the satellite and the circuits 300, 400 which conducts a direct current signal and an AC signal between the circuits 300, 400 and the satellite is attached to TB1, 2. Generally, the circuit components are shown by FIGS. 3 and 5 with commercially available component part designations. Resistance values are in ohms (1% resistors RN 55C, others ¼ watt 5% unless otherwise specified). Capacitor values are shown in microfarads, and short, thick printed circuit board lines are shown by dashed line enhancement. Plug terminal connectors are shown as identically numbered blocks, while wire connectors to the circuit board are shown as circled E designators.

The circuit 300 of FIG. 3 comprises voltage reference circuit 302, bias voltage circuit 310 and a reference temperature control feedback loop comprising feedback balanced bridge circuit 304, error amplifier circuit 306, and controlled current source circuit 308. The circuit 300 further includes a sensor control and gas measurement feedback loop comprising feedback balanced bridge circuit 312, sample and hold circuit 314, error amplifier circuit 316, comparator circuit 318, floppy triangle wave oscillator 320, active sensor bypass switch circuit 322 and duty cycle to DC converter circuit 324.

The voltage reference circuit 302 provides reference voltage primarily for the duty cycle to DC converter circuit 324 although it also provides reference voltage for a bias circuit 310. The voltage reference circuit 302 comprises voltage regulator U1, resistors R21, R4 and R5, and capacitors C2 and C3, configuration of which will depend on the actual type of device used for the voltage regulator U1. The illustrated circuit 300 uses a negative six volt, 3 terminal voltage regulator, designated 79 MO6, as manufactured by Fairchild, Motorola and National Semiconductor, and for this device, resistor R4 is replaced by a short circuit and R5 is replaced by an open circuit.

In operation, the device 10 is provided with a power supply of at least +14 volts to terminal TB1, 1, which may be externally supplied through conduit connectors as shown in FIG. 1. The negative common line of the 14 volt supply is similarly externally connected to terminal TB1, 3. The voltage regulator U1 functions to provide at its output terminal a line 6 volts below the plus 14 volt line (at the top of the schematic) for utilization by various components of the circuit 300 of FIG. 3.

A feedback loop including a first Wheatstone bridge is provided to maintain the reference sensor 24 at substantially constant temperature and comprises feedback bridge 304, error amplifier 306, and controlled current source 308. The reference sensor temperature compensation bridge 304, which is to be balanced by feedback, comprises reference resistance elements R17, R28 and R39, in addition to the reference sensor 24. The reference resistance elements may vary in resistance according to the temperature at which it is desired to operate the reference element 24 of the instrument 10. As more current goes through the reference element, its resistance will increase in view of the positive temperature coefficient of its resistance. Current is adjusted through the bridge 304 to establish the balance point of the bridge by the feedback control system, which maintains this balance in operation regardless of the ambient temperature. In the bridge 304 this balance is achieved when the ratio of the temperature dependent resistance of the reference sensor 24 to the resistance of resistor R17 will equal the ratio of R28 to R39, which in the illustrated embodiment occurs when the reference sensor 24 has a resistance of 10 ohms (at desired operating temperature).

One element of the feedback components which balance bridge 304 is the error amplifier 306. The error amplifier 306 is connected to the respective center points of each leg of the bridge 304 and functions to keep the voltages equal at the bridge center points by varying the current to the reference sensor to change its resistance. Accordingly, the error amplifier 306 functions to change the voltage occurring between the reference sensor 24 and resistor R17 and to match it up with the voltage occurring between R28 and R39. Included in the error amplifier feedback circuit 306 are resistors R38, R29, R30, capacitor C7 and operational amplifier U2 pins 12, 13 and 14. The illustrated embodiment 300 is provided, over all, with eight operational amplifier circuits, which are integrated in groups of four on two LM124 integrated circuit devices (designated "U2" or "U3" in FIG. 3) of the type sold by National Semiconductor and a number of other companies. Individual operational amplifier circuits are designated herein by device, pin and FIGURE designations in accordance with practice in the art. Operational amplifier U2, pins 12, 13, 14 functions to maintain pins 12 and 13 at the same voltage. Resistors R38 and R30 together set the gain of the error amplifier U2, pins, 12, 13, 14. Capacitor C7 and resistor R29 are feedback loop compensation components used to obtain stability of the loop.

Another component of the feedback loop is the controlled current source 308 which comprises diode CR8, transistors Q9, Q1, resistors R2, R3, R1 and R20 and a 2N4901 power transistor in a TO-3 package. The error amplifier 306 output is provided to the base of transistor Q9 creating a current output through the collector of transistor Q9, which is controlled by the value of resistor R20 and the voltage at the base of transistor Q9. This current is limited by diode CR8 so that as the error amplifier 306 searches for its proper value, it will not burn out the sensor 24 by putting too much current through it. That control current coming out of the collector of transistor Q9 causes a voltage to appear across resistor R2. That voltage is transferred also into the base of transistor Q1 and through the emitter of transistor Q1 through the base and the emitter of the TO-3 transistor which creates a voltage across resistor R1. This voltage produced across resistor R1 is changed into a current which flows through the collector of the TO-3 transistor through either the active sensor 22 and the diodes CR1 and CR2, or through the active sensor bypass switch 322 formed by transistor Q6 (which will be described in more detail hereinafter), down into the reference sensor bridge. Components CR1, CR2 and Q6 (not part of the reference sensor bridge 304) represent two alternate paths by which the current may travel from the current source output at the collector of the TO-3 transistor down into the bridge.

A bias voltage circuit 310 is provided in addition to the voltage reference circuit 302, for providing a bias voltage for the U3 operational amplifiers. The bias voltage circuit 310 utilizes the relative negative 6 volts reference output of voltage reference circuit 302, and creates a 12 volt bias voltage as shown in FIG. 3. In the circuit 310, two of the four operational amplifiers of the U2 device are used. Device U2, pins 1, 2 and 3, and U2, pins 8, 9 and 10, in addition to transistor Q2, and resistors R7, R8, R9, and R40. The bias voltage circuit 310 divides the negative 6 volts reference down to a negative 2 volts which occurs between resistor R7 and R8. The negative 2 volts is fed into the noninverting input of U2, pins 1, 2 and 3 and thus that negative 2 volts is transferred to the inverting input and also to resistor R6. The current through resistor R6 cannot go into the inverting input in the amplifier so it must flow through transistor Q2. Most of the current goes directly through transistor Q2 to the collector into resistor R40 where approximately 12 volts bias voltage is created, which is in turn fed into the noninverting input of operational amplifier U2, pins 8, 9 and 10. Device U2, pins 8, 9, 10 is connected as a voltage follower so that a low impedance 12 volt bias voltage occurs at pin 8 of device U2. The 12 volt bias voltage is provided to the circuits of integrated circuit device U3, as shown in FIG. 3.

A second Wheatstone bridge and associated control circuitry functions to keep the active sensor 22 at the same resistance as the reference sensor 24. The control system functions by varying the electrical power delivered to the active sensor 22 by periodically shunting the power around the active sensor 22 in its bridge circuit, without periodically bypassing the reference sensor component of its bridge. Accordingly, when the active sensor 22 is provided with combustion energy by the presence of a combustible gas, the circuitry is adapted to reduce the amount of electrical power fed to the active sensor 22 so that it may stay at constant temperature and thus constant resistance. The components of this active sensor control feedback loop comprise the bridge 312 which is to be balanced by feedback, sample and hold circuit 314, error amplifier 316, comparator 318, floppy triangle oscillator 320, active sensor bypass switch 322, and duty cycle to DC converter 324.

The active sensor bridge 312 to be balanced by feedback comprises the active sensor 22, the reference sensor 24 and the reference resistor R17 in one resistance leg. A third resistance parallel with the reference sensor 24 and the reference resistor R17, represented by resistor R27 is provided to accommodate manufacturing tolerances, etc. in the active and reference sensor unit 12. In this regard, the resistor R27 is provided parallel to the reference sensor so that when the first bridge 304 is balanced, the reference sensor 24 will have the proper current to keep it at the proper temperature, but the current that must flow through the active sensor 22 from the current source 308 will be about 10% greater (except when shunted) than that passing through the reference sensor 24 because a portion of this current is conducted through resistor R27. Thus, in a system where the two sensors 22, 24 have exactly the same temperature versus resistance characteristics, the active sensor 22 will have to be maintained at a duty cycle about 80% (rather than 100%) to provide balance of the bridge 312, as will be explained in more detail hereinafter. When the sensors 22, 24 don't match exactly, duty cycle variance may be utilized to accommodate such differences. The other leg of the active sensor control bridge 312 is provided by resistors R22 and R41, as shown in FIG. 3.

Because current is not continuously provided to the active sensor 22 in the bridge 312, the bridge 312 may not be tested for a balanced condition in the conventional continuous manner, and a sample and hold circuit 314 is provided to periodically sample the bridge 312 only when the active sensor is being provided with current. The sample and hold circuit 314 for the bridge 312 is provided to sample the bridge at a particular point in the discontinuous feedback cycle. More specifically, because the active sensor 22 is being switched on and off all the time, it does not continuously have appropriate bridge voltage, and to provide an accurate bridge measurement, the signal from the bridge 312 must be sampled only when there is in fact current going through the active sensor 22. The illustrated sample and hold circuit 314 is particularly adapted to provide the necessary periodic sampling of the active sensor bridge, and comprises transistor Q8, differential amplifier U3, pins 8, 9 and 10, resistor R37, diode CR6, and capacitors C8 and C9. The sample and hold circuit 314 is switched on and off by means of transistor Q8. The gate of transistor Q8 is turned on by the control input at the anode of diode CR6. A square wave control signal (as subsequently described) is applied to that input (and to the switch 322) which functions to turn on and off at the sample and hold circuit 314. When the square wave signal rises, the current from the square wave source 318 flows through diode CR6 into the gate of transistor Q8, and also to resistor R37 and capacitor C8. The role of resistor R37 and capacitor C8 is to provide a fast "turn-off", but a slow "turn-on" of the sample and hold gate. In this regard, when the square wave control signal input rises, this rise causes transistor Q8 to turn-off very rapidly, because the square wave source driving the sample and hold circuit is a low impedance source which fills capacitor C8 with charge very easily. However, when the square wave input falls to turn on transistor Q8, then diode CR6 blocks the square wave input and even though the square wave input goes down very quickly, capacitor C8 will remain high and be discharged slowly through R37. This creates a delay such that transistor Q8 turns on relatively slowly. This provides the appropriate timing in the circuit for proper sampling operation at the indicated control signal frequency. The hold capacitor is capacitor C9. Whenever transistor Q8 is closed to tap off the bridge voltage, then capacitor C9 charges up until it reaches that same bridge voltage. Then when transistor Q8 is opened, capacitor C9 holds that voltage until the next sampling cycle. Capacitor C9 is chosen to have such a value that even with the leakage current of transistor Q8 and differential amplifier U3, pin 10, it will hold the voltage for long enough to provide the stability in the circuit. The output of the sample and hold circuit 314 is provided at differential amplifier U3 pin 8 to an error amplifier circuit 316. The error amplifier 316 is accordingly effectively connected to both legs of the bridge by the sample and hold circuit 314, the one leg leading from the resistors R22 and R41 having been sampled at appropriate times by the sample and hold circuit 314, and the other leg being connected through resistor R31 directly to the center of the bridge 312 containing the active and reference sensors. Because the center of the bridge 312 is maintained at substantially constant voltage with respect to the square wave control signal frequency, no periodic sampling in respect thereto is necessary.

The error amplifier 316 comprises resistors R31, R32, R33, R34, R35, capacitors C6 and C10, diode CR7 and differential amplifier U3, pins 12, 13 and 14. Capacitor C10 functions to reduce noise at the noninverting input of differential amplifier U3, pins 12, 13 and 14. Resistors R32 and R34 determine the gain of the error amplifier U3, pins 12, 13 and 14. Capacitor C6 and resistor R33 are feedback loop compensation components which function to provide stability of the circuit feedback loop. Resistor R35 and diode CR7 form a clamp which limits the output voltage of the error amplifier 316 to a predetermined voltage so that it is not possible to go to a duty cycle of 0%, where the active sensor is always off. In such circumstances, the sample and hold circuit 314 would never sample, because it only samples during the time when the active sensor 22 is provided with current. Accordingly, clamp components R35 and CR7 are added to limit the duty cycle to prevent the active sensor from being completely turned off. The output of the error amplifier 316 provided at the clamp at the junction of resistor R35 and diode CR7, is fed into the comparator circuit 318 which generates the square wave control signal used to control the active sensor bypass switch 322 and the sample and hold circuit 314. The comparator circuit 318 also receives input from floppy triangle wave oscillator 320. The output from the floppy triangle wave oscillator 320 is used by the comparator 318 to vary the duty cycle of this control signal to the bypass switch 322 and sample and hold circuit 314. The floppy triangle wave oscillator 320 comprises resistors R36, R44, R43 and R42, capacitor C11 and operational amplifier U3, pins 1, 2 and 3. In operation, the oscillator 320 produces a wave shape at pin 2 of the operational amplifier which is roughly like a triangle wave, except that it is slightly curved (hence the designation "floppy"). The output of the error amplifier 316 from the clamp of resistor R35 and diode CR7 is compared with this triangle wave by the comparator 318. As the DC voltage output from the error amplifier 316 is changed, then a square wave output from the comparator 318 is provided which is of variable duty cycle. In this regard, sampling at the "top" of the triangle wave output of the triangle wave oscillator 320 provides a very narrow square wave output from the comparator 318, while sampling at the middle of the triangle wave provides a square wave output from the comparator 318 of approximately 50% duty cycle, and sampling at the base of the triangle wave provides a square wave output of relatively large duty cycle. Accordingly, as the duty voltage changes, the output of the error amplifier is compared with the triangular wave to produce a variable duty cycle output. This variable duty cycle output is the circuit feedback signal which functions to control the temperature of the active sensor 22.

The comparator 318 comprises operational amplifier U3, pins 5, 6 and 7. The output of the comparator 318 is a square wave which is fed back to the sample and hold circuit 314 as previously described, and which is also fed to the active sensor bypass switch 322.

The active sensor bypass switch is an important component of the feedback control loop for the active sensor of instrument 10. The active sensor bypass switch 322 comprises resistors R19, R24, R25, R26, diodes CR1 and CR2 and transistors Q6 and Q7. The purpose of resistors R24 and R26 is to form a threshold voltage so that the switch 322 will not turn on until sufficient voltage has been created at the input to the sample and hold circuit 314 such that the sample and hold circuit 314 has turned off. In this manner, it is assured that the sample and hold circuit 314 is turned off before the active sensor 22 is shorted. Then once transistors Q7 and Q6 turn on, the active sensor 22 is shorted (i.e., current is bypassed around the sensor 22). Diodes CR1 and CR2 are placed in series with the active sensor 22 (although not in any bridges) to insure that the active sensor 22 actually receives zero volts and zero current when the switch 322 is on. Transistor Q6 has a saturating voltage which is non-zero such that if only transistor Q6 were used to short the active sensor 22 a small amount of current could still flow through the sensor. Hence, by shorting out the combination of the active sensor 22 and diodes CR1 and CR2 in series, it is guaranteed that negligible current will flow through the active sensor 22 when the switch 322 is shorted. Balancing of the active sensor feedback loop involves that the active sensor 22 being at the same resistance as the reference sensor 24 plus the reference resistor R27, which is also accounted for in the value of the resistors R22 and R41 of the other leg of this bridge 312. Once a loop is established, then there will always be a certain duty cycle of current occuring across the active sensor 22 to keep the bridge 312 in balance. When combustible gas is introduced to the active sensor 22, it will be provided with additional thermal input which would tend to unbalance the bridge 312 and hence cause the duty cycle of current directed through active sensor to decrease in the total amount of electrical power fed to it (over time) to keep the bridge 312 in balance. The measurement utilization of this duty cycle change to achieve bridge balance in the illustrated embodiment 300 involves conversion of the duty cycle information to a DC quantity by the duty cycle to DC converter 324.

The illustrated duty cycle to DC converter circuit comprises resistors R23, R9, R8, R7, R11, R10, R13, R12, R14, 15, R16, diodes CR3 and CR5, transistors Q3, Q4, Q5, operational amplifier U2 pins 5, 6 and 7 and capacitor C4. The duty cycle to DC converter 324 functions in response to the duty cycle of the control signal for turning on and off of the active sensor 22. As the active sensor 22 goes on and off, transistor Q3 is turned on and off. When transistor Q3 is on, a current is provided which flows through resistor R23 to the collector of transistor Q3 and to the diodes CR3 and CR4. The amount of current flowing through diode CR4 is adjusted so that the current flowing in diode CR3, which remains, will be approximately similar to that in CR3, making the voltage drop across diodes CR3 and CR4 substantially equal and making the voltage occuring at the junction between diode CR4 and resistor R11 substantially equal to the minus 6 volts of the voltage reference, whenever transistor Q3 is on. When transistor Q3 is off, then no current will flow through resistor R11. Resistors R7, R8 and R9 form a reference divider which provides a three volt potential directed to the noninverting input of differential amplifier U2, pins 5, 6 and 7. At the inverting input of the differential amplifier, which is a current summing node, there is a constant current which is created by this three volt potential flowing through R10 and a variable current created by the variable duty cycle (on-off) of the three volt potential provided across resistor R11. This variable current and the fixed current are combined at the current summing node and occur as a voltage at the emitter of transistor Q5. This resultant voltage is provided as a DC voltage because of capacitor C4, which has an averaging or integrating effect on the variable duty cycle at the input. Resistor R13, transistors Q4 and Q5, and resistors R14, R15 and R16 form a current source, the current of which is determined by the voltage at the emitter of transistor Q5. In normal operation the emitter of transistor Q5 is designed to vary between minus 6 volts and minus 10 volts. Under such circumstances, from approximately 1 to 20 milliamperes will flow out of the collectors of transistors Q4 and Q5. This direct current then flows out through diode CR5 to the terminal transmitter cable connector TB1, 2 (connected by transmission line unit 204 or 206) to provide a measure of combustible gas concentration which is there converted to digital value and transmitted to console 200. R16 is the main resistor by which the voltage at the transistor Q5 emitter is turned into a current. Resistor R15 provides an idle current for which the voltage at the Q5 emitter is exactly six volts, then an idle current of 1 milliampere will still flow through Q5 and out to TB1, terminal 2 as an output signal of the instrument 10. This idle current may however be changed to a value outside the normal range of 1-20 millivolts under control of the remote sensor circuit illustrated in FIGS. 4 and 5. In the illustrated embodiment 400 (FIGS. 4 and 5), the sensor output current delivered to the transmitter transmission line at TB1, terminal 2 may be modified in response to several inputs to the circuit 400. The electrical connections between the sensor/transmitter circuit 300 and the remote calibration control circuit 400 are made by flexible cable connections between identically numbered terminals 1, 2, 4, 5, 7, 8 of terminal array labelled J2 on each board. In this regard, for example, as shown in FIGS. 3 and 5, the fixed volt supply line at J2, terminal 1, which in combination with the other common line at J2 terminal 8 are provided from the transmitter circuitry 300 to which the remote calibration circuitry 400 is connected and which provide directly or indirectly, power supply and various reference voltages for the circuitry 400.

The first input information channel is an input based on the amount of current flowing through the sensor and transmitter. This sensor/transmitter current is measured as a voltage across a resistor (R18) placed in series with the transmitter and sensor, as illustrated in FIG. 4. This voltage is provided as an input signal to a comparator 402. The comparator 402 functions to determine whether the current flowing through the current measuring resistor R18 (i.e., whether the sensor element current is non-functional) is within a predetermined normal range, or is in abnormal range such as would be represented by, for example, the sensor being open, to result in a dramatic decrease in current. In the illustrated embodiment, the comparator reference voltage is chosen such that the output of the comparator will change when the gas detection sensor is open (represented by a current of less than about 150 milliamperes through resistor R18). The comparator 402 provides an input to the peak detector 406, which functions to detect intermittent failure conditions which could also occur at the frequency of the bridge circuit operation in the event of a failed sensor or reference element. Accordingly, it will be appreciated that the comparator 402 and peak detector 406 function as a malfunction indicator to provide a malfunction control for the sensor/transmitter unit 10 which is responsive to a sensor current input. The comparator circuit 402 comprises operational amplifier U1, pins 8, 9 and 10, which compares the voltage across resistor R18 with a predetermined reference voltage established by buffered reference voltage operational amplifier circuitry including operational amplifier U1, pins 1, 2 and 3, together with transistor Q3. In operational mode, this circuitry establishes a current level requirement of about 150 milliamperes through resistor R18 of sensor circuit 300. If this current falls below 150 milliamperes, the output from pin 8 of operational amplifier U1, pins 8, 9 and 10 is caused to change its state to "high" (near the +14 volt supply), which causes transistor Q4 of the peak detector 406 to be "on". In order to determine a periodically failed condition which could result from disabling one of the sensor elements, and which condition would probably be at the operating frequency of the combustible gas sensor 300, the peak detector circuit 406, including transistor Q4 responds when the output at pin 8 of operational amplifier U1, pins 8, 9 and 10 is alternately high and low, the capacitor C2 maintaining the periodic high output from pin 8 to transistor Q4 in an apparent high mode, corresponding to a failed sensor condition.

The two other input channels for the circuit 400 are the "zero" and "span" input control channels which are provided by the operator upon application of the magnetic tool 11 to the hall effect sensor 416. The hall effect magnetic sensor provides an output to "zero" comparator 418 in response to application of one polarity field, and an output to span comparator 422 in response to application of the opposite field. The predetermined magnetic field strength required to activate the sensors 416 is selected to be large enough so that it is substantially greater than for forseeable natural or accidental magnetic flux densities to induce a sensor response. The zero and span hall effect sensor element U3, which is a hall effect magnetoresistor integrated circuit including power input pins 1, 4 and magnetic polarity output sensor pins 2, 3. Output pin 3 of hall magnetoresistor circuit U3 provides the input to zero comparator circuit 418 which includes operational amplifier U2, pins 5, 6 and 7, pin 7 of which provides an appropriate output signal upon application of the designated "zero" magnetic polarity to the magentoresistor U3. Pin 2 of the magnetoresistor U3 provides input to span comparator circuit 422, which includes operational amplifier U2, pins 1, 2 and 3 for similarly providing an appropriate output at pin 1 responsive to application of the "span" magnetic polarity to the magnetoresistor U3. The output from zero comparator 418 and span comparator 422 is provided through appropriate input resistors R7 and R10, respectively, to the output V-I converter 412 which comprises transistor Q2, the collector of which makes connection to the transmitter/controller signal wire of combustible gas detector transmitter circuit 300 at terminal 5 as shown in the drawings of FIGS. 3 and 5. The zero and span comparator outputs at pins 1 and 7 of operational amplifiers U2 and the peak detector transistor Q4 also provide input to transmitter output deactivator transistor Q1 through resistor R12. The collector of transistor Q1 makes connection to the combustible gas detector transmitter by means of connection J2 terminal 4, to disable the normal output current of the circuit 300 when sensor faults, zero or span input conditions are present.

The output voltage-to-current (V-I) converter 412 receives the input signals from the comparator 402 and peak detector 406, the zero comparator 418, which changes state upon application of the "zero" magnetic field, and the span comparator 422 which changes state upon application of the "span" magnetic field to the hall effect sensor 416. The transmitter output deactivator switch 414 receives the previously described terminal input signals from the sensor fault detectors 402, 406, and the zero or span comparators 418, 422. When any one of the signals is activated, whether it be the sensor failure signal, the zero sensor signal or the span signal, the transmitter output deactivator switch will be turned to an "on" state to cause the transmitter 300 current output to be turned off so that no current will flow from the transmitter back to the controller 200. Accordingly, a substitute current may be transmitted to provide information to the central control system 200 as a result of one of the input signals being present (which has also caused the normal 1-20 milliampere transmitter current to be shut off). The output voltage to current converter 412 receives the three signals from the three different input conditions of sensor fault, zero calibration and span calibration, and converts each respective input signal to a unique current for each of the three conditions, which can be appropriately detected by the control console 200.

The output signal from the V-I converter 412 is directed to J2 terminal 4 where it is connected to the transmitter-to-controller signal wire at TB1, 2.

The three input states supplied to device 412 are from sensor fault detector circuitry 402, 406, a 2 volt signal from zero comparator 418, and a 4 volt signal from span comparator 422 which cause the device 412 to generate output currents of 750, 250 and 500 microamperes, respectively. The three inputs, of course, correspond to the failure input, the zero input, and the span input signals.

The "fail" signal from the sensor current comparator 402 and peak detector 406 has the capability of overriding the "zero" and "span" signals from the comparators 418, 422, so that this condition is brought to the attention of the operator and other functions are disabled.

The output section 424 of the remote calibration circuit 400 receives an input to the terminal from the control console 200 in the form of a 20 kilohertz wave of four volts peak to peak amplitude superimposed on the DC signal conducted between the transmitter and the controller. As previously described, this AC signal can exist on the signal wire without interfering with the DC signal, so that the transmitter 300 may be in normal operation receiving the signal from the sensor and transmitting a gas concentration signal back to the controller 200 in the form of a 1-20 milliampere DC current signal. The presence of the 20 kilohertz signal corresponds to the condition of an operator receiving an LED signal from the central controller. The AC detector 426 determines the presence or non-presence of AC on the signal wire. When the AC signal from the controller 200 is present on the signal wire, the signal is detected by detector 426, which causes comparator 428 to activate the LED indicator 15, as previously described.

The AC detector 424 is adapted to detect the 20 KHz signal provided at J2 terminal 5 by means of capacitor C1 as shown in FIG. 5. The AC signal on capacitor C1 is rectified by diode CR3 and provided as an input to the comparator circuit 428 comprising operational amplifier U1, pins 5, 6 and 7, which in turn provides an output at pin 7 responsive to such AC signal on the transmitter and controller signal wire. The output from pin 7 of operational amplifier U1, pins 5, 6 and 7 causes LED indicator 15 (DS1) to flash in response to an AC signal applied from the controller to the controller/transmitter signal wire, as previously described.

As previously discussed, the remote calibration sensor circuit 400 is enclosed in a sealed explosion-proof housing 16, which is shown in cross section in FIG. 6, which further depicts the top side of the printed circuit board 62 for the circuitry of FIG. 5. The placement of the various circuit elements of circuit 400 shown in FIG. 5 is shown on pc board 62 together with the printed circuit connections therefor on the reverse side of the printed circuit board. The housing 16 is formed of a nonferromagnetic material, which in the illustrated embodiment is aluminum. The base 66 of the housing 16 is provided with appropriate threads for insertion into the coupling of connector box 18 which houses the combustible gas detector and the transmitter circuitry 300. The base 66 of the printed circuit board 62 is provided with appropriate terminal connectors with pins numbered thereon for a flexible terminal connector with the combustible gas detector transmitter circuitry.

The distal end 68 of the aluminum housing 16 is provided with internal thread connections to receive an explosion-proof seal with a threaded bolt 70 which has a central transparent glass element 72 fused therein. The sealing bolt element 70 is placed, as shown in FIG. 6, within a protective recess 74 adapted to receive the calibration magnet tool 11 shown in FIG. 1. Upon insertion of the magnet into the recess 74, the magnetic field interacts with the hall magnetic resistor U3. The LED device 15 (DS1), which signals the operator, is placed to be readily viewed by the operator through the fused glass window 72 at the central portion of the sealing bolt 70. An end view of the printed circuit board 62 is shown in FIG. 7, to further illustrate the compact nature of the circuit design.

The printed circuit board 62 fits snugly within the axial bore of the aluminum housing 16, and is retained by the resilient O-ring 65 at the distal end of the internal housing bore, and a spring loaded ring clip element 67 which is engageable in an appropriate recess in the bore.

Illustrated in FIG. 8 is a flow chart for the operation of the control console 200. The console 200 may be, an appropriate computer system, and the flow chart logic may utilize any suitable software. In order to calibrate a given sensor, the operator will first set the state for a calibration of the sensor state equals one by appropriate software. As indicated, the controller circuitry will read the sensor input data, which is stored in the controller in digital form, and first seeks to determine when the "zero" end of the magnetic calibration tool is applied to the sensor upon which the LED 15 is turned on and the calibration made variable is set to 1 as indicated in FIG. 8. Upon removal of the zero end of the magnetic tool 11, which in the illustrated embodiment must take place within 16 cycles of the test program (each cycle takes approximately 6 seconds) for a total of 96 seconds. After removal of the zero end of the calibration tool, the calibration mode variable is set to 2 and calibration gas must be applied to the sensor, and the sensor must achieve a stable reading (i.e., the digital data from the sensor stored in the controller must achieve 3 consecutive identical readings) within 96 seconds. After establishing a stable reading, the LED 15 is turned off and the calibration mode is set to 3, to cause the controller 200 to require the application of the span end of the magnetic calibration tool within 96 seconds. After application of the span tool, the calibration mode is set to 5 to engage the span calibration cycle of the system. The appropriate span calibration gas must be applied and a stable reading must be transmitted to the controller within a predetermined time (here 96 seconds), after which the LED is again turned off, and the system pauses for 96 seconds before permitting reinitiation of the calibration cycle. Whenever any of the procedures aborts the calibration, the LED 15 will be directed to blink 8 times to indicate an error, under program control, as previously described.

In use, an operator at the remote location will apply a magnet 11 (as a method of entering input signals into the remote calibration terminal 16) to select and transmit either "zero" or "span" signals, which are a request to the control console 200 to calibrate the sensor. The operator will put the zero end of the calibration magnet 11 to the center of the remote calibration terminal 16 interface surface, which will cause substitution of a 250 microampere signal for normal transmitter signal. The normal signal will always exceed one milliampere, as previously discussed. Upon receiving the 250 microampere signal, the control console 200 is adapted to send back a 20 kHz signal to cause an indication via the LED 15 that zeroing may proceed.

When the user puts the zero end of the magnet on, the control console 200 monitors the current output signal from the unit 10. If the sensor signal is stable and the signal is not changing, the steady signal will be recognized as a baseline or "zero" as commanded by the calibration technician.

In the case of zeroing in the presence of combustible gas, the operator would apply a zero gas such as compressed nitrogen or combustibles free compressed air in a bottle, to the snesor terminal 12. This is one reason that the control console 200 should best be adapted to test for a steady signal, because the sensor 12 may be changing down to a true zero level in the presence of the zero gas, the console unit 200 should wait for a stable signal before acknowledging and storing a proper zero baseline for that sensor instrument.

Upon storing the zero baseline signal value (which may be stored as a digital value in the control console 202), the controller 200 will send back a steady LED indication for a few seconds to acknowledge the successful zero calibration to the operator. If the LED goes out after a few seconds, that will mean to the operator that he has been successfully zeroed. If the LED remains flashing, however, it will mean to the operator that the system was unable to zero the sensor. One of the reasons for such failure could include a signal that was not in a predetermined range, or a signal that was drifting, and therefore should not be considered a valid baseline value. However, having successfully carried out a zero calibration, the operator may proceed to request a "span" calibration by putting the span end of the magnet 11 on the interface surface of the remote calibration terminal 16.

For a span calibration request, the operator similarly applies a "span" gas having a predetermined combustible gas concentration. The illustrated sensor 12 will produce a time varying signal approaching its steady-state value for the "span" gas. The LED 15 will remain on until the sensor signal due to the span gas has become stable, at which point the control console 200 may then calibrate the span (if possible) and then the LED light will be turned off. The span value is stored as a span calibration factor and may be appropriately applied with the stored zero value for each respective sensor/transmitter unit to subsequent signals obtained from the sensor in its gas detecting mode. The normalized measurement values thus obtained may be recorded or displayed as desired, and may be used to set off appropriate alarms.

Accordingly, it will be appreciated that the remote calibration system illustrated in FIG. 1 has a number of desirable features. It is not necessary to classify a test areas and then open an electrical box that contains electrical circuitry that would not normally be exposed to the atmosphere. Further, it is not necessary to remove the sensor box cover for carrying out a remote calibration, which is instead initiated by simply bringing the calibration magnet in the vicinity of the calibration terminal to cause the zero or span calibration cycles to begin. The calibration may be carried out with only the magnet and calibration gas supply, and there are no manual adjustments necessary at the remote sensor site. On-site operator discretion (and concomitant potential for error) are reduced.

It will further be appreciated that while the present invention has been particularly described with respect to one specific embodiment, various modifications and adaptations will be apparent based on the present disclosure, and such modifications and adaptations are intended to be within the spirit and scope of the present invention.

Various of the features of the invention are set forth in the following claims.

What is claimed is:

1. Apparatus for remote calibration of combustible gas measurement apparatus or the like comprising a sealed sensor transmitter unit and a remotely located control apparatus for said unit, said sensor transmitter unit comprising means for detecting the presence of combustible gas and for transmitting an output signal responsive to the concentration thereof to said remotely located control apparatus, means for determining whether said output signal is within a predetermined operative signal range, and for transmitting a sensor fault signal to said remotely located control apparatus, zero calibration input channel means for generating and transmitting a zero calibration initiating signal to said remotely located control apparatus in response to an externally applied activation signal, span calibration means for generating and transmitting a span calibration initiating control signal to said remotely located control station in response to an externally applied activation signal, and means for receiving an acknowledgement signal from said remotely located control station, and said remotely located control apparatus comprising means for receiving said output signal, zero signal and span signal, means for transmitting an acknowledgement signal to said sensor unit, and means for storing zero and span response calibration values of said sensor unit upon initiation of respective zero and span calibration cycles by said zero calibration means and span calibration means.

2. Apparatus in accordance with claim 1 wherein said zero and span signal generation means are respectively responsive to the application of magnetic fields of opposite polarity.

3. Apparatus in accordance with claim 1 wherein said output signal is a current signal in a predetermined current range, and wherein said fault, zero and span calibration signals are current signals outside of said predetermined range of said output signal.

4. Apparatus in accordance with claim 3 wherein said remotely located control station comprises analog to digital converter means for converting current signals from said sensor unit representative of combustible gas concentration, sensor fault, zero calibration initiation or span calibration initiation into digital form.

5. Apparatus in accordance with claim 4 wherein said remotely located control station comprises means for storing digital values representing a zero calibration baseline value for said sensor unit, and a span calibration sensitivity value for said sensor unit.

6. Apparatus in accordance with claim 5 wherein said apparatus comprises a plurality of individual sensor transmitter units each independently communicating with and controlled by said remotely located control apparatus.

7. Apparatus in accordance with claim 5 wherein said sensor fault signal, zero calibration signal, or span calibration signal displaces said combustible gas concentration signal.

8. A method for remotely calibrating the output signal of a combustible gas detector or the like comprising the steps of;

applying an external zero calibration initiation signal to a receiver for said zero calibration initiation signal contained in an explosion proof enclosure and transmitting a zero calibration signal to a remotely located control station;

measuring the combustible gas concentration at a sampling location and transmitting an ouput signal representing zero combustible gas concentration to said remotely located control station as a zero calibration factor;

detecting the stability of said zero output signal and storing the value of said signal upon said stability detection, to represent zero baseline response of the detector;

applying an external span calibration initiation signal to a receiver for said signal contained in an explosion-proof enclosure and transmitting to said control station a calibration initiation signal;

measuring at said location the concentration of a known calibration gas containing a predetermined concentration of combustible gas for transmitting to said remotely located control station and transmitting an output signal representing said known concentration of combustible gas; and storing the value of said predetermined concentration signal as a span calibration factor.

9. A method in accordance with claim 8 further including the steps of transmitting an acknowledgement signal from said control station to said sampling location upon storage of said zero calibration value, and transmitting an acknowledgement signal from said control station to said sampling station upon storage of said span calibration factor.

10. A method in accordance with claim 9 wherein a calibration abort signal is transmitted from said control station to said sampling station upon failure to detect a stable zero or span calibration value.

* * * * *